United States Patent [19]
Balasubramaniam

[11] Patent Number: 6,046,167
[45] Date of Patent: Apr. 4, 2000

[54] PEPTIDE YY ANALOGS

[75] Inventor: Ambikaipakan Balasubramaniam, Cincinnati, Ohio

[73] Assignee: University of Cincinnati, Cincinnati, Ohio

[21] Appl. No.: 09/047,986

[22] Filed: Mar. 25, 1998

[51] Int. Cl.$^7$ .......................... A61K 38/07; A61K 38/08; A61K 38/10; C07C 229/32; C07K 7/08
[52] U.S. Cl. ..................... 514/13; 514/14; 514/15; 514/16; 514/17; 514/18; 530/326; 530/327; 530/328; 530/329; 530/330; 562/443
[58] Field of Search ..................... 562/441, 443; 514/567, 9, 10, 11, 13, 14, 15, 16, 17, 18, 19, 20; 530/317, 318, 321, 326, 327, 328, 329, 330, 331

[56] References Cited

U.S. PATENT DOCUMENTS

| | | | |
|---|---|---|---|
| 4,871,550 | 10/1989 | Millman | 424/601 |
| 5,376,640 | 12/1994 | Miyazaki et al. | 514/12 |
| 5,397,803 | 3/1995 | Smith et al. | 514/563 |
| 5,574,010 | 11/1996 | McFadden | 514/12 |
| 5,604,203 | 2/1997 | Balasubramaniam | 514/12 |
| 5,670,482 | 9/1997 | Daniels et al. | 514/12 |
| 5,830,434 | 11/1998 | Taylor et al. | 424/9.2 |
| 5,885,958 | 3/1999 | Zadina et al. | 514/9 |

FOREIGN PATENT DOCUMENTS

92/09628  6/1992  WIPO .

OTHER PUBLICATIONS

Balasubramaniam et al. High yield synthesis of pseudopeptide . . . Leiden: ESCOM Science Publ. Peptides: Chemistry, Structure and Biol. pp. 553–555, 1994.
Chemical Abstract: 70: 37018h, 1969.
Galuez et al. Cobalt–Mediated Alkylation . . . Tet. Lett. vol. 37, No. 34, pp. 6197–6200, 1996.
Roberts et al, Basic Principles of Organic Chemistry, 2nd ed. Menlo Park: W.A. Benjamin, Inc, pp. 1208–1210, 1977.
Balasubramaniam, A., et al., Neuropeptides (1989) 14, 209–212.
Laburthe, M., et al., Endocrinology, vol. 118, No. 5, pp. 1910–1917. (1986).
Tatemoto, K., Proc. Natl. Acad. Sci. USA, vol. 79, pp. 2514–2518, Apr. 1982.
Tatemoto, K., Proc. Natl. Acad. Sci. USA, vol. 79, pp. 5485–5489, Sep. 1982.
Ekblad, E., Neuroscience, vol. 20, No. 1, pp. 169–188, 1987.
Laburthe, M., Trends Endocrinol. Metab., vol. 1, No. 3, pp. 168–174, 1990.
Cox, H.M., et al., Br. J. Pharmacol. 101, pp. 247–252, 1990.
Cox, H.M., et al. J. of Physiology, 1988, vol. 398, pp. 65–80.
Cox, H.M., et al., Peptides, vol. 12, pp. 323–327, 1991.
Friel, D.D., et al., Br. J. Pharmacol. (1986), vol. 88, pp. 425–431.
Lundberg, J.M., et al., Proc. Natl. Acad. Sci. USA, vol. 79, pp. 4471–4475, Jul. 1982.
Playford, R.J., et al., The Lancet, 1990; 335: 1555–1557.
MacFadyen, R.J., et al., Neuropeptides 7: 219–227, 1986.
Adrian, T.E., et al., Gastroenterology, 1985; 89: 1070–1077.
Servin, A.L., et al., Endocrinology, vol. 124, No. 2, pp. 692–700. (1989).
Bilchik, A.J., et al., Gastroenterology, vol. 104. No. 4, Part 2, A 236. (1993).
Balasubramaniam, A., et al., Peptide Research, vol. 1, No. 1, 1988, pp. 32–35.
Voisin, T., et al., J. of Biol. Chem., vol. 268, No. 27, Sep. 25, pp. 20547–20554, 1993.
Valet, P., et al., J. Clin. Invest., vol. 85, Jan. 1990, pp. 291–295.

*Primary Examiner*—Jeffrey E. Russel
*Attorney, Agent, or Firm*—Frost & Jacobs LLP

[57] ABSTRACT

The invention provides analogs of PYY. The invention also provides compositions and methods useful for controlling biological activities such as cell proliferation, nutrient transport, lipolysis, and intestinal water and electrolyte secretion.

26 Claims, No Drawings

PEPTIDE YY ANALOGS

STATEMENT AS TO FEDERALLY SPONSORED RESEARCH

This invention was made in part with Government funding, NIH grant number GM47122, and the Government therefore has certain rights in the invention.

BACKGROUND OF THE INVENTION

This invention relates to peptides which are useful as therapeutic agents in the treatment of gastroenterological disorders.

Peptide YY (PYY) is a 36-residue peptide amide isolated originally from porcine intestine, and localized in the endocrine cells of the gastrointestinal tract and pancreas (Tatemoto et al. *Proc. Natl. Acad. Sci.* 79:2514, 1982). Peptide YY has N-terminal and C-terminal tyrosine amides; accordingly, these two tyrosines give PYY its name (Y represents the amino acid tyrosine in peptide nomenclature). In addition., PYY shares a number of central and peripheral regulatory roles with its homologous peptide Neuropeptide Y (NPY), which was originally isolated from porcine brain (Tatemoto, *Proc. Natl. Acad. Sci.* 79:5485, 1982). PYY is localized in intestinal cells; NPY, in contrast, is present in the submucous and myenteric neurons which innervate the mucosal and smooth muscle layers, respectively (Ekblad et al. *Neuroscience* 20:169, 1987). Both PYY and NPY are believed to inhibit gut motility and blood flow (Laburthe, *Trends Endocrinol. Metab.* 1:168, 1990), and they are also thought to attenuate basal (Cox et al. *Br. J Pharmacol.* 101:247, 1990; Cox et al. *J. Physiol.* 398:65, 1988; Cox et al. *Peptides* 12:323, 1991; Friel et al. *Br. J. Pharmacol.* 88:425, 1986) and secretagogue-induced intestinal secretion in rats (Lundberg et al. *Proc. Natl. Acad. Sci USA* 79:4471, 1982; Playford et al. *Lancet* 335:1555, 1990) and humans (Playford et al., supra), as well as stimulate net absorption (MacFadyen et al. *Neuropeptides* 7:219, 1986). Elevated plasma PYY levels have been reported in individuals suffering from several conditions that cause diarrhea (Adrian et al. *Gastroenterology* 89:1070, 1985). Taken together, these observations suggest that PYY and NPY are released into the circulation after a meal (Adrian et al. *Gastroenterology* 89:1070, 1985; Balasubramaniam et al. *Neuropeptides* 14:209, 1989), and, thus, may play a physiological role in regulating intestinal secretion and absorption, serving as natural inhibitors of diarrhea.

A high affinity PYY receptor system which exhibits a slightly higher affinity for PYY than NPY has been characterized in rat intestinal epithelia (Laburthe et al. *Endocrinology* 118:1910, 1986; Laburthe, *Trends Endocrinol. Metab.* supra) and shown to be negatively coupled to adenylate cyclase (Servin et al. *Endocrinology* 124:692, 1989). Consistently, PYY exhibited greater antisecretory potency than NPY in voltage clamped preparations of rat small intestine (Cox et al. *J. Physiol.* supra), while C-terminal fragments of NPY were found to be less effective in their antisecretory potency than PYY (Cox et al. *Br. J. Pharmacol.* supra). Structure-activity studies using several partial sequences have led to the identification of PYY(22–36) as the active site for interacting with intestinal PYY receptors (Balsubramaniam et al. *Pept. Res.* 1:32, 1988).

In addition, PYY has been implicated in a number of physiological activities including nutrient uptake (see, e.g., Bilcheik et al. *Digestive Disease Week* 506:623, 1993), cell proliferation (see, e.g., Laburthe, *Trends Endocrinol. Metab.* 1:168, 1990; Voisin et al. *J. Biol. Chem,* 1993), lipolysis (see, e.g., Valet et al., *J. Clin. Invest.* 85:291, 1990), and vasoconstriction (see, e.g., Lundberg et al.,*Proc. Natl. Acad. Sci., USA* 79:4471, 1982).

The amino acid sequences of porcine and human PYY are as follows:

porcine PYY: YPAKPEAPGEDASPEELSRYYASL-RHYLNLVT RQRY, (SEQ ID NO:1)

human PYY: YPIKPEAPGEDASPEELNRYYASL-RHYLNLVTRQRY. (SEQ ID NO:2) The amino acid sequences for dog PYY and for rat PYY are the same as that of porcine YYY.

U.S. Pat. No. 5,604,203, issued Feb. 18, 1997, to the present inventor generically discloses PYY analogs which encompass the compounds of this invention of the formula:

N-α-Ac-[Nle$^{24,28,30}$, Trp$^{27}$, Nva$^{31}$, ψ$^{35/36}$]PYY(22–36)-NH$_2$, (SEQ ID NO:3)

N-α-Ac-[Nle$^{24,28}$, Trp$^{27,30}$, Nva$^{31}$, ψ$^{35/36}$]PYY(22–36)-NH$_2$, (SEQ ID NO:4)

N-α-Ac-[Nle$^{24,28,30}$, Phe$^{27}$, Nva$^{31}$, ψ$^{35/36}$]PYY(22–36)-NH$_2$, (SEQ ID NO:5)

N-α-Ac-[Nle$^{24,28}$, Phe$^{27}$, Trp$^{30}$, Nva$^{31}$, ψ$^{35/36}$]PYY(22–36)-NH$_2$, (SEQ ID NO:6)

N-α-Ac-[Trp$^{30}$, ψ$^{35/36}$]PYY(25–36)-NH$_2$, (SEQ ID NO:7)

N-α-Ac-[Trp$^{30}$]PYY(25–36)-NH$_2$, (SEQ ID NO:8)

N-α-Ac-[Nle$^{24,28}$, Trp$^{30}$, Nva$^{31}$, ψ$^{35/36}$]PYY(22–36)-NH$_2$ (SEQ ID NO:9) and N-α-Ac-[Nle$^{28}$, Trp$^{30}$, Nva$^{31}$, ψ$^{35/36}$]PYY(22–36)-NH$_2$, (SEQ ID NO:10) wherein ψ in the foregoing formulas is —CH$_2$—NH—. The compound N-α-Ac-[Nle$^{24,28}$, Trp$^{30}$, Nva$^{31}$, ψ$^{35/36}$]PYY(22–36)-NH$_2$ (SEQ ID NO:9) shows unexpectedly enhanced activity as a more potent and longer lasting antisecretory agent when compared to PYY.

SUMMARY OF THE INVENTION

In one aspect, the present invention is directed to the peptides of the formula:

N-α-R$^1$-[Nle$^{24,28,30}$, Trp$^{27}$, Nva$^{31}$, ψ$^{35/36}$]PYY(22–36)-NH$_2$,

N-α-R$^1$-[Nle$^{24,28}$, Trp$^{27,30}$, Nva$^{31}$, ψ$^{35/36}$]PYY(22–36)-NH$_2$,

N-α-R$^1$-[Nle$^{24,28,30}$, Phe$^{27}$, Nva$^{31}$, ψ$^{35/36}$]PYY(22–36)-NH$_2$,

N-α-R$^1$-[Nle$^{24,28}$, Phe$^{27}$, Trp$^{30}$, Nva$^{31}$, ψ$^{35/36}$]PYY(22–36)-NH$_2$,

N-α-R$^1$-[Trp$^{30}$, ψ$^{35/36}$]PYY(25–36)-NH$_2$,

N-α-R$^1$-[Trp$^{30}$]PYY(25–36)-NH$_2$,

N-α-R$^1$-[Nle$^{24,28}$, Trp$^{30}$, Nva$^{31}$, ψ$^{35/36}$]PYY(22–36)-NH$_2$ and N-α-R$^1$-[Nle$^{28}$, Trp$^{30}$, Nva$^{31}$, ψ$^{35/36}$]PYY(22–36)-NH$_2$ or a pharmaceutically-acceptable salt thereof, wherein R$^1$ is H, (C$_1$–C$_{12}$)alkyl or (C$_1$–C$_{12}$)acyl; and ψ is a pseudopeptide bond selected from the group consisting of —CH$_2$—NH—, —CH$_2$—S—, —CH$_2$—CH$_2$—, —CH$_2$—O— and —CH$_2$—CO—.

Preferred compounds of the immediately foregoing group of compounds are where R$^1$ is acetyl and ψ is —CH$_2$—NH—.

A preferred group of compounds of the foregoing group of compounds is where the compound is selected from a group consisting of N-α-Ac-[Nle$^{24,28,30}$, Trp$^{27}$, Nva$^{31}$, ψ$^{35/36}$]PYY(22–36)-NH$_2$, (SEQ ID NO:3)

N-α-Ac-[Nle$^{24,28}$, Trp$^{27,30}$, Nva$^{31}$, ψ$^{35/36}$]PYY(22–36)-NH$_2$, (SEQ ID NO:4)

N-α-Ac-[Nle$^{24,28,30}$, Phe$^{27}$, Nva$^{31}$, ψ$^{35/36}$]PYY(22–36)-NH$_2$, (SEQ ID NO:5)

N-α-Ac-[Nle$^{24,28}$, Phe$^{27}$, Trp$^{30}$, Nva$^{31}$, ψ$^{35/36}$]PYY(22–36)-NH$_2$, (SEQ ID NO:6)
N-α-Ac-[Trp$^{30}$, ψ$^{35/36}$]PYY(25–36)-NH$_2$, (SEQ ID NO:7)
N-α-Ac-[Trp$^{30}$]PYY(25–36)-NH$_2$ (SEQ ID NO:8) and
N-α-Ac-[Nle$^{28}$, Trp$^{30}$, Nva$^{31}$, ψ$^{35/36}$]PYY(22–36)-NH$_2$, (SEQ ID NO:10) or a pharmaceutically acceptable salt thereof.

A most preferred compound of this invention is the compound of the formula N-α-Ac-[Nle$^{24,28}$, Trp$^{30}$, Nva$^{31}$, ψ$^{35/36}$]PYY(22–36)-NH$_2$ (SEQ ID NO:9) or a pharmaceutically acceptable salt thereof.

In another aspect, this invention is directed to a compound of the formula (A),

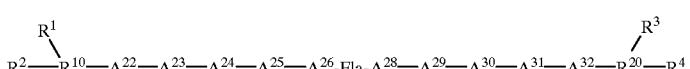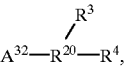

(A)

having one or two pseudopeptide bonds where each pseudopeptide bond is independently selected from the group consisting of —CH$_2$—NH—, —CH$_2$—S—, —CH$_2$—CH$_2$—, —CH$_2$—O— and -CH$_2$—CO—; wherein $R^{10}$ is a chain of 0–5 amino acids, inclusive, where the N-terminal amino acid is bonded to $R^1$ and $R^2$ by the side chain of the N-terminal amino acid or by the nitrogen of the amino group of the N-terminal amino acid;

$R^{20}$ is a chain of 0–4 amino acids, inclusive, where the C-terminal amino acid is bonded to $R^3$ and $R^4$ by the side chain of the C-terminal amino acid or by the carbon of the carboxyl group of the C-terminal amino acid;

$R^1$, $R^2$, $R^3$ and $R^4$ are each independently selected from the group consisting of H, (C$_1$–C$_{12}$)alkyl, (C$_6$–C$_{18}$)aryl, (C$_1$–C$_{12}$)acyl, phenyl(C$_1$–C$_{12}$)alkyl and ((C$_1$–C$_{12}$)alkyl)$_{1-5}$-phenyl;

$A^{22}$ is an aromatic amino acid, Ala, Aib, Anb, N-Me-Ala or is deleted;

$A^{23}$ is Ser, Thr, Ala, N-Me-Ser, N-Me-Thr, N-Me-Ala or is deleted;

$A^{24}$ is Leu, Ile, Nle, Val, Trp, Gly, Aib, Anb, N-Me-Leu or is deleted;

$A^{25}$ is Arg, Lys, homo-Arg, diethyl-homo-Arg, Lys-pε-NH-Z, Orn or is deleted;

$A^{26}$ is His, Thr, 3-Me-His, 1-Me-His, β-pyrazolylalanine, N-Me-His, Arg, Lys, homo-Arg, diethyl-homo-Arg, Lys-ε—NH-Z, Orn or is deleted;

$A^{28}$ is Leu, Ile, Nle, Val, Trp, Aib, Anb or N-Me-Leu;
$A^{29}$ is Asn, Ala, Gln, Gly, Trp or N-Me-Asn;
$A^{30}$ is Leu, Ile, Nle, Fla, Val, Trp, Aib, Anb or N-Me-Leu;
$A^{31}$ is Val, Nva, Ile, Trp, Aib, Anb or N-Me-Val; and
$A^{32}$ is Thr, Ser, N-Me-Ser or N-Me-Thr;

where Z for each occurrence is independently selected from the group consisting of H, (C$_1$–C$_{10}$)alkyl and (C$_6$–C$_{18}$)aryl; or a pharmaceutically acceptable salt thereof.

A preferred group of compounds of the immediately foregoing group of compounds is where $R^{10}$ is $A^{17}$-$A^{18}$-$A^{19}$-$A^{20}$-$A^{21}$;

where $A^{17}$ is Cys, Leu, Ile, Val, Nle, Nva, Aib, Anb or N-Me-Leu;
$A^{18}$ is Cys, Ser, Thr, N-Me-Ser or N-Me-Thr;
$A^{19}$ is Arg, Lys, homo-Arg, diethyl-homo-Arg, Lys-ε-NH-R$^5$, Cys or Orn;
$A^{20}$ is an aromatic amino acid or Cys;
$A^{21}$ is an aromatic amino acid or Cys;

$R^{20}$ is $A^{33}$-$A^{34}$-$A^{35}$-$A^{36}$, $A^{33}$ is Arg, Lys, homo-Arg, diethyl-homo-Arg, Lys-ε-NH-R$^5$, Cys or Orn;
$A^{34}$ is Cys, Gln, Asn, Ala, Gly, N-Me-Gln, Aib or Anb;
$A^{35}$ is Arg, Lys, homo-Arg, diethyl-homo-Arg, Lys-ε-NH-R$^5$, Cys or Orn; and
$A^{36}$ is an aromatic amino acid or Cys;

where R$^5$ for each occurrence is independently selected from the group consisting of
H, (C$_1$–C$_{10}$)alkyl and (C$_6$–C$_{18}$) aryl.

A preferred group of compounds of the foregoing group of compounds are the compounds of the formula N-α-Ac-[Fla$^{27}$)]PYY(25–36)-NH$_2$ and N-α-Ac-[Fla$^{27}$]PYY(22–36)-NH$_2$ or a pharmaceutically acceptable salt thereof.

In another aspect, this invention provides a compound selected from the group consisting of:

(I), (R$^1$R$^2$)-A$^1$-A$^2$-A$^3$-A$^4$-A$^5$-A$^6$-A$^7$-A$^8$-A$^9$-A$^{10}$-R$^{30}$,

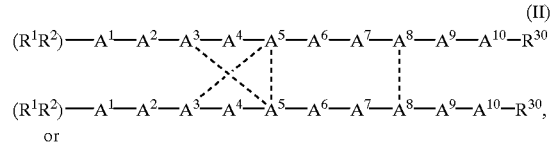

(II)

(III) (R$^1$R$^2$)-[A$^5$-A$^6$-A$^7$-A$^8$-A$^9$-A$^{10}$]$_m$R$^{30}$, or a pharmaceutically acceptable salt thereof wherein
------represents an optional bond between the amino acids shown connected where each bond is independently selected from the group consisting of —S—S— only when the amino acids connected are Cys-Cys, —CO—NH—, —CH$_2$—NH— and

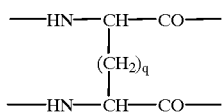

provided that when the optional bond is

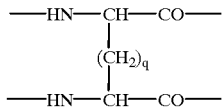

it replaces the two amino acids that the optional bond is attached to; q is 1–4;
m is 1 to 4;
$R^{30}$ is OH or —O—R$^1$, provided that when A$^1$ to A$^7$ are deleted then R$^{30}$ is also NH—R$^1$, where
$R^{30}$ is attached to the carbon atom of the carboxyl of the C-terminal amino acid;
$R^1$ and $R^2$ for each occurrence are each independently selected from the group consisting of H, (C$_1$–C$_{12}$)alkyl, (C$_6$–C$_{18}$)aryl, (C$_1$–C$_{12}$)acyl, phenyl(C$_1$–C$_{12}$)alkyl and ((C$_1$–C$_{12}$)alkyl)$_{1-5}$-phenyl where R$^1$ and R$^2$ are attached to the nitrogen of the amine of the N-terminal amino acid;
A$^1$ is deleted or D- or L- of the following amino acids: Trp, Tyr, Fla, Bth, Nal, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^2$ is deleted or D- or L- of the following amino acids: Ile, Val, Leu, Nle, Anb, Aib, Pro, Gln or Asn;

$A^3$ is deleted or D- or L- of the following amino acids: Asn, Gln, Glu, Asp, Orn, Lys, Dpr or Cys;

$A^4$ is deleted or D- or L- of the following amino acids: Ile, Val, Leu, Nle, Anb, Aib or Pro;

$A^5$ is deleted or D- or L- of the following amino acids: Ile, Val, Leu, Nle, Anb, Aib, Pro, Glu, Asp, Orn, Lys, Dpr or Cys;

$A^6$ is deleted or D- or L- of the following amino acids: Thr, Ser, Trp, Tyr, Fla, Bth, Nal, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^7$ is deleted or D- or L- of the following amino acids: Arg, Lys, homo-Arg, dialkyl-homo-Arg, Lys-ε-NH-$R^7$ or Orn;

$A^8$ is deleted or D- or L- of the following amino acids: Nva, Val, Ile, Leu, Nle, Anb, Aib, Pro, Gln, Asn, Glu, Asp, Orn, Lys, Dpr or Cys;

$A^9$ is deleted or D- or L- of the following amino acids: Arg, Lys, homo-Arg, dialkyl-homo-Arg, Lys-ε-NH-$R^7$ or Orn; and $A^{10}$ is deleted or D- or L- of the following amino acids: Tyr, Trp, Fla, Bth, Nal, Tic, Tic-OH, Dip, Bip, tyramine or optionally substituted Phe where the Phe is optionally substituted with one to five substituents selected from the group consisting of $(C_1-C_4)$alkyl, halo, $(C_1-C_4)$alkoxy, amino and nitro, or the corresponding decarboxylated optionally substituted Phe;

where $R^7$ for each occurrence is independently selected from the group consisting of $H_1$ $(C_1-C_{10})$alkyl and $(C_6-C_{18})$ aryl, provided that not all of $A_1$ to $A_{10}$ are deleted at the same time.

A preferred group of compounds of the immediately foregoing group of compounds is (SEQ ID NO:11)
H—Ile—Asn—Pro—Ile—Tyr—Arg—Leu—Arg—Tyr—OMe, (SEQ ID NO:12)
H—Ile—Asn—Pro—Cys—Tyr—Arg—Leu—Arg—Tyr—Ome
                    |
H—Ile—Asn—Pro—Cys—Tyr—Arg—Leu—Arg—Tyr—Ome, (SEQ ID NO:13)
H—Cys—Tyr—Arg—Leu—Arg—Tyr—OMe
    |
H—Cys—Tyr—Arg—Leu—Arg—Tyr—OMe, (SEQ ID NO:14)
H—Ile—Asn—Pro—NH—CH—CO—Tyr—Arg—Leu—Arg—Tyr—OMe
                    |
                  (CH$_2$)$_4$
                    |
H—Ile—Asn—Pro—NH—CH—CO—Tyr—Arg—Leu—Arg—Tyr—OMe, H—NH—CH—CO-Tyr-Arg-Leu-Arg-Tyr-OMe
        |
      (CH$_2$)$_4$
        |
H—NH—CH—CO-Tyr-Arg-Leu-Arg-Tyr-OMe (SEQ ID NO:15) and H-[Tyr-Arg-Leu-Arg-Tyr]$_2$-OMe, (SEQ ID NO:16) or a pharmaceutically acceptable salt thereof.

Another preferred group of compounds of the group of compounds consisting of compounds (I), (II), (III) and (IV) is the group of compounds consisting of $(R^1R^2)$—Cys—Arg—Tyr—NH$_2$
        |
$(R^1R^2)$—Cys—Arg—Tyr—NH$_2$, $(R^1R^2)$—NH—CH—CO—Arg—Tyr—NH$_2$
            |
          (CH$_2$)$_4$
            |
$(R^1R^2)$—NH—CH—CO—Arg—Tyr—NH$_2$ and H-[-Arg-Tyr]$_2$—NH$_2$, (SEQ ID NO:20) or a pharmaceutically acceptable salt thereof.

In another aspect, this invention is directed to a pharmaceutical composition comprising any one or more of the compounds described hereinabove or a pharmaceutically acceptable salt thereof, and a pharmaceutically acceptable carrier.

In another aspect, this invention provides a method of decreasing excess intestinal water and electrolyte secretion in a mammal in need thereof, said method comprising administering to said mammal an effective amount of one or more compounds described hereinabove or a pharmaceutically acceptable salt thereof.

In another aspect, this invention provides a method of regulating cell proliferation in a mammal in need thereof, said method comprising administering to said mammal an effective amount of one or more compounds described hereinabove or a pharmaceutically acceptable salt thereof. A preferred method of this method is where the type of cell proliferation that is regulated is gastrointestinal cell or epithelial cell.

In another aspect, this invention provides a method of augmenting nutrient transport in a mammal in need thereof, said method comprising administering to said mammal an effective amount of one or compounds described hereinabove or a pharmaceutically acceptable salt thereof.

In another aspect, this invention provides a method of regulating lipolysis in a mammal in need thereof, said method comprising administering to said mammal an effective amount of one or more compounds described hereinabove or a pharmaceutically acceptable salt thereof.

In another aspect, this invention provides a method of regulating blood flow in a mammal in need thereof, said method comprising administering to said mammal an effective amount of one or more compounds described hereinabove or a pharmaceutically acceptable salt thereof.

In another aspect, this invention provides the compound of the formula

[Chemical structure: fluorene with CH$_2$-CH(NH$_2$)-CO$_2$H substituent]

DETAILED DESCRIPTION

As set forth above and for convenience in describing this invention, the conventional and nonconventional abbreviations for the various amino acids are used. They are familiar to those skilled in the art, but for clarity are listed below. All peptide sequences mentioned herein are written according to the usual convention whereby the N-terminal amino acid is on the left and the C-terminal amino acid is on the right, unless noted otherwise. A short line between two amino acid residues indicates a peptide bond.

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Fla=9-Fluorenylalanine
Orn=Ornithine
Nal=2-Napthylalanine
Nle=Norleucine
Nva=Norvaline
Thi=2-Thienylalanine
Pcp=4-Chlorophenylalanine
Bth=3-Benzothienyalanine
Bip=4,4'-Biphenylalanine
Tic=Tetrahydroisoquinoline-3-carboxylic acid
Tic-OH=7-Hydroxy-tetrahydroisoquinoline-3-carboxylic acid
Aib=Aminoisobutyric acid
Anb=α-Aminonormalbutyric acid
Dip=2,2-Diphenylalanine
Thz=4-Thiazolylalanine
Dpr=1,2-Diamino propionic acid The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. An example of a procedure for obtaining a pharmaceutically acceptable salt of a compound of this invention, more particularly the HCl salt, is as follows. A purified peptide is dissolved in 0.1% HCl—$H_2O$, loaded onto a semipreparative reverse phase column (250×10 mm, 10 $\mu$M particle size, 300A pore size), and eluted with a gradient of 0–100% 0.1% HCl—$CH_3CN$ in 0.1% HCl—$H_2O$. The fractions containing the peptide peak are combined, concentrated and lyophilized to obtain the HCl salt of the peptide.

A compound of the present invention can be made into compositions in the form of a liquid, pill, tablet, or capsule for oral administration; a liquid capable of being administered nasally as drops or spray or a liquid for intravenous, subcutaneous, parenteral, intraperitoneal or rectal administration. The therapeutic composition can also be in the form of an oil emulsion or dispersion in conjunction with a lipophilic salt such as pamoic acid, or in the form of a biodegradable sustained-release composition for subcutaneous or intramuscular administration.

The compounds of the invention exhibit a broad range of biological activities related to their antisecretory and antimotility properties. The compounds suppress gastrointestinal secretions by direct interaction with epithelial cells or, perhaps, by inhibiting secretion of hormones or neurotransmitters which stimulate intestinal secretion. The compounds of the invention may also control intestinal blood flow which in turn may modulate intestinal hydrostatic pressure in favor of net water absorption.

The compounds of the invention are especially useful in the treatment of any number of gastrointestinal disorders that are associated with excess intestinal electrlytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g. Harrison's principles of Internal Medicine, McGraw Hill Inc., New York, 12th ed.). Examples of infectious diarrhea include, without limitation, acute viral diarrhea, acute bacterial diarrhea (e.g., salmonella, campylobacter, and clostridium) or diarrhea due to protozoal infections, or travellers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera. Furthermore, the compounds of the invention can be used to treat intestinal dysfunction in patients with Acquired Immune Deficiency Syndrome (AIDS), especially during cachexia.

The compounds of the invention are also useful for inhibiting small intestinal fluid and electrolyte secretion, and augmenting nutrient transport, as well as increasing cell proliferation in the gastrointestinal tract, regulating lipolysis in, e.g., adipase tissue and regulating blood flow in a mammal.

The compounds of the invention are advantageous because they are truncated versions of the natural PYY peptide; thus, the shorter peptide not only facilitates easier synthesis and purification of the compounds, but also improves and reduces manufacturing procedures and expenses. Moreover, a shorter PYY compound is advantageous because such peptides will interact solely with PYY receptors and not with homologous receptors such as NPY Y1, Y3 and Y-5; thus, minimizing unwanted agonist or antagonist side reactions. Another class of compounds which are selective to pancreatic polypeptide (PP) receptors denoted by Y-4 may also be used to control intestinal dysfunctions under various conditions.

The peptides of the present invention may be synthesized by any techniques that are known to those skilled in the peptide art. An excellent summary of the many techniques so available may be found in *Solid Phase Peptide Synthesis* 2nd ed. (Stewart, J. M. and Young, J. D. Pierce Chemical Company, Rockford, Ill., 1984).

The peptides of described in the Examples below are synthesized as follows. Peptide synthesis is performed on an Applied Biosystems Model 430A synthesizer (PE Applied Biosystems, Foster City, Calif.) Amino acid and sequence analyses are carried out using Waters Pico-Tag and Applied Biosystems Model 470A instruments (PE Applied Biosystems, Foster City, Calif.), respectively. Peptides are purified using a Waters Model 600 solvent delivery system equipped with a Model 481 Spectrophotometer and U6K injector (Waters Instruments, Milford, Mass.) according to standard protocols such as those described in Balasubramaniam et al., Pept. Res. 1:32, 1988. Peptide masses are determined according to standard methods, such as electrospray or laser desorption methods. All Boc-L-amino acid derivatives and Boc-D-amino acid derivatives, solvents, chemicals and resins can be obtained commercially and used without further purification.

Peptides are synthesized on an automated Applied Biosystem Model 430A synthesizer using t-BOC amino acids protected with benzyl or halobenzyl side chain protecting groups in conjunction with either paramethylbenzhydrylamine resin (MBHA) to obtain peptide amides (e.g. Examples 1–10 below) or Merrifield resin to obtain peptide acids or O-methyl esters (e.g. Examples 11–17 below). MBHA resin (0.45 mmol, —NH$_2$ group) or the Merrifield resin (containing the 0.45 mmol C-terminal amino acid) is placed in the reaction vessel of the synthesizer and the amino acids are sequentially coupled as preformed 1-HOBT esters (4.4 equivalents).

Introduction of pseudobonds such as —CH$_2$—NH— (Examples 1–5, 7 and 8) is carried out manually according to the procedures of Saski and Coy, *Peptides* 8, pp. 119–121, 1987, the contents of which are incorporated herein by reference. Accordingly, a t-Boc-amino acid aldehyde obtained by reducing N-methoxy-N-methylamide derivatives of Boc-amino acids with LiAlH$_4$, as described by Fehrentz and Castro, *Synthesis*, pp.676–679, 1987, the contents of which are incorporated herein by reference, is reacted immediately with the α-amino group of the peptide attached to the resin in DMF containing 1.0% HOAC in the presence of an equivalent amount of NaBH$_3$CN. At the end of the reaction, the presence of secondary amine is verified with ninhydrin (wine-red color). The secondary amine formed is then blocked by reacting with 2 equivalents of Z(2-Cl)OSU, 2 equivalents of HOBT and 4 equivalents of diisopropylethylamine until the ninhydrin gives a yellow color. The resin is then reintroduced into the reaction vessel, and automated synthesis is resumed.

Dimerization with di-Boc-Cys or di-Boc-diamino suberic acid is also carried out manually. The peptide resin with free amino group is reacted with 0.5 equivalents of di-Boc-Cys (e.g. Examples 12 and 13) or di-Boc-diamino suberic acid (e.g. Examples 14 and 15) in the presence of 2 equivalents each of HOBT, DCC and DIPEA until the ninhydrin test is negative, (see *Anal. Biochem.*, 34, pp. 595–597, 1970). Coupling times vary between 24–72 hours. At the end, the resin is reintroduced into the reaction vessel of the synthesizer and automated synthesis resumed.

At the end of peptide synthesis, the t-Boc group is removed and in some cases (e.g., Examples 1–10) the free alpha amino group is acylated with acetic anhydride (about 2 equivalents) until the ninhydrin test is negative.

Peptide resin (about 1.0 g) is then reacted with HF (10 ml) containing p-cresol (about 0.8 g) for about 45 minutes at about $-2°$ to $-4°$ C. (see Balasubramaniam et al., *Peptide Research* 1: 32, 1988). The HF is evacuated, and the residue transferred to a fritted filter funnel with diethylether, washed repeatedly with diethylether and the free peptide is extracted with acetic acid (2×10 ml) and lyophilized. The peptide is purified by semi-preparative HPLC as described by Balasubramaniam et al., *Peptide Research* 1:32, 1988.

The methyl-esters of a peptide of this invention can be synthesized, for example by the following method. Fmoc-amino acids with t-butyl based side chain protecting groups are assembled automatically as described above for t-Boc synthesis on either hydroxymethybenzoyl-resin (HMBA) or Merrifield resin. The protected peptide is then cleaved from the resin as methyl ester using 10% Et$_3$N-methanol. The side chain protecting groups are then removed with TFA containing 5% water and 5% phenol. If the peptides contain Cys, Trp, or Met, 2.5 ethane dithiol is also added to TFA. The peptide methyl ester is precipitated with ether, filtered, washed with ether and dried.

EXAMPLES 1–10

Examples 1–10 were synthesized according to the procedure described hereinabove, where ψ in the formula is —CH$_2$NH—.

| Ex. # | Peptide Formula | Mass Spec. |
|---|---|---|
| 1 | N-α-Ac-[Nle$^{24,28,30}$, Trp$^{27}$, Nva$^{31}$, ψ$^{35/36}$]PYY(22–36)-NH$_2$ (SEQ ID NO: 3) | 1939.9 |
| 2 | N-α-Ac-[Nle$^{24,28}$, Trp$^{27,30}$, Nva$^{31}$, ψ$^{35/36}$]PYY(22–36)-NH$_2$ (SEQ ID NO: 4) | 1901.5 |
| 3 | N-α-Ac-[Nle$^{24,28,30}$, Phe$^{27}$, Nva$^{31}$, ψ$^{35/36}$]PYY(22–36)-NH$_2$ (SEQ ID NO: 5) | 2013.1 |
| 4 | N-α-Ac-[Nle$^{24,28,}$, Phe$^{27}$, Trp$^{30}$, Nva$^{31}$, ψ$^{35/36}$]PYY(22–36)-NH$_2$ (SEQ ID NO: 6) | 1974.3 |
| 5 | N-α-Ac-[Trp$^{30}$, ψ$^{35/36}$]PYY(25–36)-NH$_2$ (SEQ ID NO: 7) | 1781.8 |
| 6 | N-α-Ac-[Trp$^{30}$]PYY(25–36)-NH$_2$ (SEQ ID NO: 8) | 1731.9 |
| 7 | N-α-Ac-[Nle$^{24,28}$, Trp$^{30}$, Nva$^{31}$, ψ$^{35/36}$]PYY(22–36)-NH$_2$ (SEQ ID NO: 9) | 1990.6 |
| 8 | N-α-Ac-[Nle$^{28}$, Trp$^{30}$, Nva$^{31}$, ψ$^{35/36}$]PYY(22–36)-NH$_2$ (SEQ ID NO: 10) | 1989.1 |
| 9 | N-α-Ac-[Fla$^{27}$]PYY(25–36)-NH$_2$ (SEQ ID NO: 17) | 1733.7 |
| 10 | N-α-Ac-[Fla$^{27}$]PYY(22–36)-NH$_2$ (SEQ ID NO: 18) | 2004.3 |

EXAMPLES 11–17

Examples 11–17 can be synthesized according to the procedure described hereinabove.

| Ex. # | Peptide Formula | Molecular Weight |
|---|---|---|
| 11 | H—Ile—Asn—Pro—Ile—Tyr—Arg—Leu—Arg—Tyr—OMe (SEQ ID NO: 11) | 1222.46 |
| 12 | H-Ile-Asn-Pro-Cys-Tyr-Arg-Leu-Arg-Tyr-OMe<br>\|<br>H-Ile-Asn-Pro-Cys-Tyr-Arg-Leu-Arg-Tyr-OMe (SEQ ID NO: 12) | 2422.88 |

| Ex. # | Peptide Formula | Molecular Weight |
|---|---|---|
| 13 | H-Cys-Tyr-Arg-Leu-Arg-Tyr-OMe<br>\|<br>H-Cys-Tyr-Arg-Leu-Arg-Tyr-OMe (SEQ ID NO: 13) | 1774.12 |
| 14 | H-Ile-Asn-Pro-NH—CH—CO-Tyr-Arg-Leu-Arg-Tyr-OMe<br>            \|<br>         (CH$_2$)$_4$<br>            \|<br>H-Ile-Asn-Pro-NH—CH—CO-Tyr-Arg-Leu-Arg-Tyr-OMe (SEQ ID NO: 14) | 2386.70 |
| 15 | H—NH—CH—CO-Tyr-Arg-Leu-Arg-Tyr-OMe<br>         \|<br>      (CH$_2$)$_4$<br>         \|<br>H—NH—CH—CO-Tyr-Arg-Leu-Arg-Tyr-OMe (SEQ ID NO: 15) | 1737.94 |
| 16* | H-Ile-Glu-Pro-Dpr-Tyr-Arg-Leu-Arg-Tyr-OMe<br>              ✕<br>H-Ile-Glu-Pro-Dpr-Tyr-Arg-Leu-Arg-Tyr-OMe (SEQ ID NO: 19) | 2383.90 |
| 17 | H—[Tyr—Arg—Leu—Arg—Tyr]$_2$—OMe | 1536.81 |

*Where the bond between Glu and Dpr in Example is —CO—NH—.

EXAMPLE 18

Example 18 was synthesized according to the method described hereinabove using the appropriate amino acids:

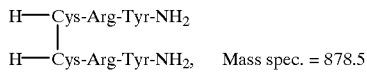

H—Cys-Arg-Tyr-NH$_2$
  \|
H—Cys-Arg-Tyr-NH$_2$,    Mass spec. = 878.5

EXAMPLE 19

Example 19 was synthesized according to the method described hereinabove using the appropriate amino acids:

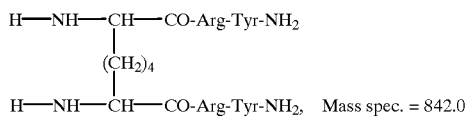

H—NH—CH—CO-Arg-Tyr-NH$_2$
         \|
      (CH$_2$)$_4$
         \|
H—NH—CH—CO-Arg-Tyr-NH$_2$,   Mass spec. = 842.0

EXAMPLE 20

Example 20 was synthesized according to the method described hereinabove using the appropriate amino acids:
H-[-Arg-Tyr]$_2$-NH$_2$, (SEQ ID NO:20) Mass spec.=656.8.

Example 21

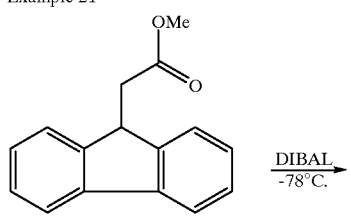

DIBAL
-78°C.

-continued

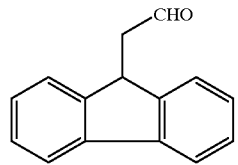

To a solution of methyl 9-fluoreneacatate (2.38 g, 10.0 mMol, 1.0 eq.) in dry toluene was added dropwise DIBAL (1.0M solution in toluene, 12 ml, 1.2 eq.) at about −78° C. The resulting mixture was stirred at about −78° C. for about 4 hours, then quenched with saturated aqueous NaHCO$_3$. The aqueous layer was extracted with ethyl acetate (3×). The combined organic phases were washed with H$_2$O (2×), and brine(1×), dried over anhydrous sodium sulfate, and concentrated in reduced pressure to afford a colorless oil. The crude product was purified by flash chromatography (silica gel, eluted by 4:1 of hexanes and ethyl acetate) to provide about 1.62 g of an oil as the product. Yield: 78%.

Alternatively, the aldehyde can be and was synthesized as follows. Et$_3$N (2 mmol) was added to a solution of (9-fluorenyl)acetic acid (2 mmol) in THF (10 ml), and the solution was cooled to about −5° C. Isobutylchloroformate (2.4 mmol) was then added and the solution was stirred at about 0–5° C. for about 20 min at which time the reaction was complete as judged by TLC (thin layer chromatography). N-methoxy-N-methylamine (2.2 mmol) and Et$_3$N (2.2 mmol) in THF (10 ml) was then added to the above solution, and stirred at about 0° C. for about 30 min, and then at room temperature for about 4 hr. at which time the reaction was complete (TLC). THF was removed and the residue was partitioned in EtOAc & water (50 ml ea). The organic layer was separated, and the aqueous phase of each extracted twice with EtOAc (20 ml×2), and the combined organic layers were washed with 5% acetic acid, 5% NaHCO$_3$ and brine, dried over MgSO$_4$ and evaporated. The residue was purified in a silica gel column (2:1 hexane/ EtOAc) to get an oily product. (540 mg, 90%). 9-Fluorenylacetly-N-methylamide(2 mmol) in THF (10 ml) was added to a solution of $LiAlH_4$ (5 mmol in THF, 10 ml), and the solution was stirred for about 20 min at room temperature. 20 ml of 0.2 N $KHSO_4$ was added and the THF evaporated. The residue was extracted with EtOAc (3×30 ml), and the combined organic layer, washed with 5% acetic acid, 5% $NaHCO_3$ and brine, dried over $MgSO_4$ and evaporated. The oily product 330 mg, 78%) obtained was used without further purification.

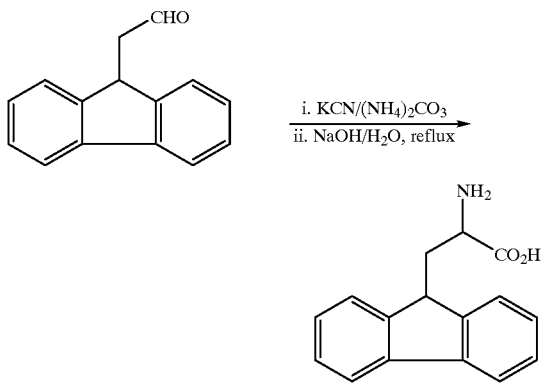

To a solution of 9-fluoreneacetaldehyde (1.04 g, 5.0 mMol, 1.0eq.), from the above reaction, in ethyl alcohol (15 ml) was added $H_2O$ (15 ml), KCN (1.3 g, 20.0 mMol, 4.0 eq.), and $(NH_4)_2CO_3$ (4.8 g, 50.0 mMol, 10.0 eq.). The resulting mixture was warmed to about 60° C. for about 6 hours, then cooled to room temperature. The product was precipitated, and purified by preparative TLC (eluted by 4:1 hexanes and EtOAc) to afford 850 mg white solid as the product. Yield: 75%. The above product was hydrolyzed with 40%(w/w) NaOH by refluxing for about 24 hours, then neutralized with 6N HCl to about pH=3, to provide the amino acid.

Purified peptides were found to be>96% homogeneous by analytical reversed phase chromatography and, in addition, had the expected amino acid composition and masses. The free peptides which are not acylated were further characterized by sequence analysis. The overall yields of the peptides were in the range of 10% to 30%.

Binding Studies: Preparation of $^{125}I$-PYY labeled only at $Tyr^{36}$ and rat jejunal epithelial plasma membranes are performed according to standard methods (see, e.g., Laburthe et al. *Endocinology*, supra; Servin et al. supra; Voisin et al. *Ann. N. Y. Acad. Sci.* 611:343, 1990). Binding experiments are conducted in a total volume of 0.25 ml 60 mM HEPES buffer, pH 7, containing 2% bovine serum albumin (BSA), 0.1% bacitracin, 5 mM $MgCl_2$ and 0.05 nM $^{125}I$-PYY with or without competing peptides. Bound and free peptides are separated by centrifugation at 20,000×g for about 10 min. Non-specific $^{125}I$-PYY binding is determined in the presence of 1 μM unlabeled PYY represented 10% of the total binding. SK-N-MC cells can be obtained from the ATCC (American Type Culture Collection, Rockville, Md.) and SK-N-BE2 cells can be obtained from the Sloan-Kettering Institute, New York, N.Y. The binding studies with SK-N-MC and SK-N-BE2 cells are carried out according to the published procedures of Balasubramaniam et al. (J. Med. Chem., 39:1142–1147, 1996), the contents of which are incorporated herein by reference.

Short Circuit Current Measurements: The antisecretory effects of the peptides of this invention are investigated by measuring the short-circuit current (SCC) in rat jejunal mucosa mounted in an Ussing chamber and automatically voltage clamped as described by Cox et al. (*J. Physiol.* supra). Strips of mucosa are placed between two halves of perspex Ussing chambers (window size, 0.6 $cm^2$) containing oxygenated (95% $O_2$/5% $CO_2$) Krebs-Henseleit solution (NaCl, 117 mM, KCl 4.7 mM, $CaCl_2$, 2.5 mM; $MgSO_4$ 1.2 mM, $NaHCO_3$ 24.8 mM and glucose 11.1 mM), pH 7.4, 37° C. Routinely, four preparations of jejunum are obtained from each animal and these exhibited comparable potential differences and SCC, but they are not paired. Preparations are automatically voltage clamped using a W-P dual voltage clamp and the SCC displayed continuously on pen recorders. Once a stable baseline SCC is reached, peptides are added to the basolateral reservoir only, and cumulative concentration-response profiles constructed.

Data Analyses: All points in a binding experiment are the mean of at least three experiments performed in duplicate. For clarity, the SEMs in the binding experiments are less than 10%. Values of changes in SCC are quoted as μA/0.6 $cm^2$ mean±1SEM from between 3 and 7 different preparations. $EC_{50}$ values are calculated from pooled cumulative concentration—response curves using an iterative curve fitting program. Comparison of data groups (SCC recordings) are made using unpaired Student's t-tests where a p value <0.5 is considered statistically significant.

To study the effects on intestinal water and sodium absorption ileal Thiry-Vela fistulae (TVF) are constructed in dogs and assessments are performed at different time points after postoperative recovery.

Materials And Methods: Female mongrel dogs (n=6; about 20 kg) (Martin Creek Kennels, Williford, Ariz.) undergo creation of an ileal TVF after being fasted with free access to water 24 h prior to operation. Following induction of anesthesia with sodium pentobarbital (30 mg/kg; Abbott, Chicago, Ill.) and infusion of systemic antibiotics (Batryl 60 mg/kg; Haver, Shawnee, Kans.) dogs undergo a midline laparotomy. A TVF is created by isolating a neurovascularly intact ileal segment (25 cm in length) 10 cm proximal to the ileocecal valve that is brought through the anterior abdominal wall and sutured to the skin with 3-0 absorbable suture as cephaled (proximal) and caudad (distal) stomas. Intestinal continuity is restored with end to end anastomoses with interrupted 3-0 silk in a double-layered fashion. Batryl is continued for 5 days post-operatively and the dogs are allowed to recover for 2 weeks; TVF are flushed routinely with 50 ml of normal saline starting 2 weeks after operation. All studies are approved by the Institutional Animal Care and Use Committee and performed in accordance with their recommendations.

Peptide preparation: A stock solution of either PYY (Bachem Bioscience Inc., Philadelphia, Pa.), or the peptide to be tested is prepared by first dissolving the amount of PYY or a peptide needed for the study in 1 ml of sterile water with 0.1% (w/vol) bovine serum albumin (BSA) (Sigma Chemical Co., St. Louis, Mo.) and then diluted to the required concentration with saline containing 0.1% BSA. Equal portions of this solution, sufficient for a single experiment for all dogs are stored in plastic vials at about −70° C.

Perfusate preparation: The TVF is perfused with an isotomic solution during the experimental protocol and consisted of the following: 140 mM $Na^+$, 5.2 mM $K^+$, 119.8 mM $Cl^-$, 25 mM $HCO_3^-$, 1.2 mM $Ca^{2+}$, 1.2 mM $Mg^{2+}$, 2.4 mM $HPO_4^{2-}$, 0.4 mM $H_2PO_4^-$, 10 mM glucose, and a nonabsorbable agent, 5 g/L polyethylene glycol (PEG; MW=4000) (Sigma Chemical Co., St. Louis, Mo.) supplemented with 10 μCl $[^{14}C]$ PEG (MW=4000) (NEN Life Sciences Inc., Boston, Mass.); the perfusate was maintained at a pH of about 7.4 and a temperature of about 37° C.

Experimental design: Starting 2 weeks post-operatively, a series of independent experiments are performed in which all dogs are studied with a single peptide and then allowed to recover for at least 48 hours prior to being studied with the next peptide until each peptide has been tested. Cumulatively, PYY is tested twice (at two different dosages) and each PYY analog is tested once in all dogs. For all experiments, dogs are fasted overnight with free access to water and then placed in Pavlonian harnesses in the standing position. TVF are cannulated proximally and distally with 12-French Foley catheters.

Catheter balloons are inflated with 3.5 ml of water to maintain intraluminal position and TVF are flushed with at least 500 ml of saline (37° C.) until the return from the distal catheter was clear. Dog hindleg intravenous (iv) catheters are infused at a constant rate of 60 ml/hr throughout the experiment with saline alone or saline with either PYY or a PYY analog. Concomitantly, perfusate is introduced through the TVF at a constant rate of 2.0±0.2 ml/hr for a 20-min washout period. Once a steady state is achieved, perfusate is collected every 15 min during a 60-min baseline period, a 60-min treatment period, and a 30-min post-treatment period. In the 60-min treatment period, dogs received either PYY (100 pmole/kg or 200 pmole/kg), or a PYY analog (200 pmole/kg) iv; the 100 pmole/kg dose of PYY has been shown to produce serum levels equal to that of the post-prandial state during which endogenous PYY secretion is maximal, and the superphysiologic 200 pmole/kg dose of PYY or PYY analog has also been described previously, see Bilchik, A. J., et al., Gastroenterology, 105:1441–1448, 1993.

Absorption Studies: Water flux ($FH_{H2O}$) and sodium flux ($F_{Na+}$) were determined using [$^{14}$C]PEG activity and measured by liquid scintillation counting (Model LS6000; Beckman, Irvine, Calif.). Sodium concentration ([Na$^+$]) was measured by a sodium electrode (Model 86-11; Orion Research Incorporated Laboratory Products Group, Boston, Mass.). The following formulas were used to calculate $F_{H2O}$, $F_{Na+}$, and percent recovery of perfusate. $F_{H2O}$ ($\mu$l/min)= infusate flow rate×1- ([$^{14}$C]PEG$_{infusate}$/[$^{14}$C]PEG$_{effluent}$)
$F_{Na+}$=($\mu$Eq/min)=infusate flow rate×([Na$^+$]$_{infusate}$-([Na$^+$]$_{effluent}$ -[$^{14}$C]PEG$_{infusate}$/[$^{14}$C]PEG$_{effluent}$))
Percent Recovery=([$^{14}$C]PEG$_{effluent}$×volume$_{effluent}$)/([$^{14}$C] PEG$_{infusate}$×volume$_{infusate}$)×100%

Only data with a 100±10% recovery from each experimental period are used in the calculations of flux. Water and sodium absorptions are then calculated by integrating the respective fluxes over 30-min intervals during a baseline period (−60 to −30 and −30 to 0 min intervals), a treatment period (0 to 30 and 30 to 60 min intervals), and a post-treatment period (60 to 90 min interval).

Statistical Analysis: Flux and absorption data is expressed as mean±SEM. Absorption data is analyzed using analysis of variance (ANOVA) for a two factor experiment with repeated measures on time. Tukey's least significant difference procedure is used for multiple comparisons. Baseline flux data is analyzed using ANOVA with Fisher's least significant difference procedure for multiple comparisons. For both ANOVA, a p value<0.05 is considered significant. For comparison of peak flux to baseline flux in each treatment group, Student's t-test for independent means of baseline and peak fluxes at the 0.05 level of significance is used.

In the practice of the method of the present invention, an effective amount of any one of the peptides of this invention or a combination of any of the peptides of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally ( e.g., by suppositories or washings), transdermally (e.g., skin electroporation) or by inhalation (e.g., by aerosol), and in the form or either solid, liquid or gaseous dosage, including tablets and suspensions. The administration can be conducted in a single unit dosage form with continuous therapy or in a single dose therapy ad libitum.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in *Remington's Pharmaceutical Sciences* by E. W. Martin. Such compositions will, in any event, contain an effective amount of the active compound together with a suitable carrier so as to prepare the proper dosage form for proper administration to the recipient.

The dose of the compound of the present invention for treating the above-mentioned disorders varies depending upon the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". Thus, a typical administration is oral administration or Thus, a typical administration is oral administration or parenteral administration. The daily dose in the case of oral administration is typically in the range of 0.1 to 100 mg/kg body weight, and the daily dose in the case of parenteral administration is typically in the range of 0.001 to 50 mg/kg body weight.

What is claimed is:

1. A compound selected from the group consisting of:
N-α-R$^1$-[Nle$^{24,28,30}$, Trp$^{27}$, Nva$^{31}$, ψ$^{35/36}$]PYY(22–36)-NH$_2$,
N-α-R$^1$-[Nle$^{24,28}$, Trp$^{27,30}$, Nva$^{31}$, ψ$^{35/36}$]PYY(22–36)-NH$_2$,
N-α-R$^1$-[Nle$^{24,28,30}$, Phe$^{27}$, Nva$^{31}$, ψ$^{35/36}$]PYY(22–36)-NH$_2$,
N-α-R$^1$-[Nle$^{24,28}$, Phe$^{27}$, Trp$^{30}$, Nva$^{31}$, ψ$^{35/36}$]PYY(22–36)-NH$_2$,
N-α-R$^1$-[Trp$^{30}$, ψ$^{35/36}$]PYY(25–36)-NH$_2$,
N-α-R$^1$-[Trp$^{30}$]PYY(25–36)-NH$_2$,
N-α-R$^1$-[Nle$^{24,28}$, Trp$^{30}$, Nva$^{31}$, ψ$^{35/36}$]PYY(22–36)-NH$_2$ and
N-α-R$^1$-[Nle$^{28}$, Trp$^{30}$, Nva31, ψ$^{35/36}$]PYY(22–36)-NH$_2$ or a pharmaceutically-acceptable salt thereof,
wherein R$^1$ is H, (C$_1$–C$_{12}$)alkyl or (C$_1$–C$_{12}$)acyl; and
ψ is a pseudopeptide bond selected from the group consisting of —CH$_2$—NH—, —CH$_2$—S—, —CH$_2$—CH$_2$—, —CH$_2$—O— and —CH$_2$—CO—.

2. A compound according to claim 1 where R$^1$ is acetyl and ψ is —CH$_2$—NH—.

3. A compound according to claim 2 where the compound is selected from a group consisting of
N-α-Ac-[Nle$^{24,28,30}$, Trp$^{27}$, Nva$^{31}$, ψ$^{35/36}$]PYY(22–36)-NH$_2$(SEQ ID NO:3),
N-α-Ac-[Nle$^{24,28}$, Trp$^{27,30}$, Nva$^{31}$, ψ$^{35/36}$]PYY(22–36)-NH$_2$(SEQ ID NO:4),
N-α-Ac-[Nle$^{24,28,30}$, Phe$^{27}$, Nva$^{31}$, ψ$^{35/36}$]PYY(22–36)-NH$_2$(SEQ ID NO:5),
N-α-Ac-[Nle$^{24,28}$, Phe$^{27}$, Trp$^{30}$, Nva$^{31}$, ψ$^{35/36}$]PYY(22–36)-NH$_2$(SEQ ID NO:6),
N-α-Ac-[Trp$^{30}$, ψ$^{35/36}$]PYY(25–36)-NH$_2$(SEQ ID NO:7),
N-α-Ac-[Trp$^{30}$]PYY(25–36)-NH$_2$(SEQ ID NO:8), and
N-α-Ac-[Nle$^{28}$, Trp$^{30}$, Nva$^{31}$, ψ$^{35/36}$]PYY(22–36)-NH$_2$ (SEQ ID NO:10) or a pharmaceutically acceptable salt thereof.

4. The compound according to claim 2 of the formula N-α-Ac-[Nle$^{24,28}$, Trp$^{30}$, Nva$^{31}$, ψ$^{35/36}$]PYY(22–36)-NH$_2$ or a pharmaceutically acceptable salt thereof.

5. A pharmaceutical composition comprising a compound of claim 1 or a pharmaceutically acceptable salt thereof, and a pharmaceutically acceptable carrier.

6. A method of decreasing excess intestinal water and electrolyte secretion in a mammal in need thereof, said method comprising administering to said mammal an effective amount of a compound of claim 1 or a pharmaceutically acceptable salt thereof.

7. A method of regulating cell proliferation in a mammal in need thereof, said method comprising administering to said mammal an effective amount of a compound of claim 1 or a pharmaceutically acceptable salt thereof.

8. A method of claim 7, wherein said cell is a gastrointestinal cell.

9. A method of claim 7, wherein said cell is an epithelial cell.

10. A method of augmenting nutrient transport in a mammal in need thereof, said method comprising administering to said mammal an effective amount of a compound of claim 1 or a pharmaceutically acceptable salt thereof.

11. A method of regulating lipolysis in a mammal in need thereof, said method comprising administering to said mammal an effective amount of a compound of claim 1 or a pharmaceutically acceptable salt thereof.

12. A method of regulating blood flow in a mammal in need thereof, said method comprising administering to said mammal an effective amount of a compound of claim 1 or a pharmaceutically acceptable salt thereof.

13. A compound of the formula (A),

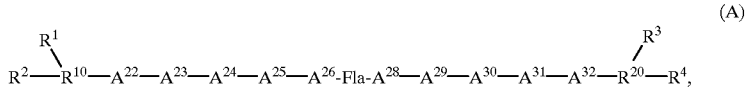

(A)

having one or two pseudopeptide bonds where each pseudopeptide bond is independently selected from the group consisting of —CH$_2$—NH—, —CH$_2$—S—, —CH$_2$—CH$_2$—, —CH$_2$—O— and —CH$_2$—CO—;
wherein
R$^{10}$ is a chain of 0–5 amino acids, inclusive, where the N-terminal amino acid is bonded to R$^1$ and R$^2$ by the side chain of the N-terminal amino acid or by the nitrogen of the amino group of the N-terminal amino acid;
R$^{20}$ is a chain of 0–4 amino acids, inclusive, where the C-terminal amino acid is bonded to R$^3$ and R$^4$ by the side chain of the C-terminal amino acid or by the carbon of the carboxyl group of the C-terminal amino acid;

$R^1$, $R^2$, $R^3$ and $R^4$ are each independently selected from the group consisting of H, $(C_1-C_{12})$alkyl, $(C_6-C_{18})$aryl, $(C_1-C_{12})$acyl, phenyl$(C_1-C_{12})$alkyl and $((C_1-C_{12})$alkyl$)_{1-5}$-phenyl;

$A^{22}$ is an aromatic amino acid, Ala, Aib, Anb, N-Me-Ala or is deleted;

$A^{23}$ is Ser, Thr, Ala, N-Me-Ser, N-Me-Thr, N-Me-Ala or is deleted;

$A^{24}$ is Leu, Ile, Nle, Val, Trp, Gly, Aib, Anb, N-Me-Leu or is deleted;

$A^{25}$ is Arg, Lys, homo-Arg, diethyl-homo-Arg, Lys-ϵ-NH-Z, OM or is deleted;

$A^{26}$ is His, Thr, 3-Me-His, 1-Me-His, β-pyrazolylalanine, N-Me-His, Arg, Lys, homo-Arg, diethyl-homo-Arg, Lys-ϵ-NH-Z, Orn or is deleted;

$A^{28}$ is Leu, Ile, Nle, Val, Trp, Aib, Anb or N-Me-Leu;

$A^{29}$ is Asn, Ala, Gln, Gly, Trp or N-Me-Asn;

$A^{30}$ is Leu, Ile, Nle, Fla, Val, Trp, Aib, Anb or N-Me-Leu;

$A^{31}$ is Val, Nva, Ile, Trp, Aib, Anb or N-Me-Val; and $A^{32}$ is Thr, Ser, N-Me-Ser or N-Me-Thr;

where Z for each occurrence is independently selected from the group consisting of H, $(C_1-C_{10})$alkyl and $(C_6-C_{18})$aryl;

or a pharmaceutically acceptable salt thereof.

14. A compound according to claim 13 wherein $R^{10}$ is $A^{17}$-$A^{18}$-$A^{19}$-$A^{20}$-$A^{21}$, where $A^{17}$ is Cys, Leu, Ile, Val, Nle, Nva, Aib, Anb or N-Me-Leu;

$A^{18}$ is Cys, Ser, Thr, N-Me-Ser or N-Me-Thr;

$A^{19}$ is Arg, Lys, homo-Arg, diethyl-homo-Arg, Lys-ϵ-NH-$R^5$, Cys or Orn;

$A^{20}$ is an aromatic amino acid or Cys;

$A^{21}$ is an aromatic amino acid or Cys;

$R^{20}$ is $A^{33}$-$A^{34}$-$A^{35}$-$A^{36}$, where $A^{33}$ is Arg, Lys, homo-Arg, diethyl-homo-Arg, Lys-ϵ-NH-$R^5$, Cys or Orn;

$A^{34}$ is Cys, Gln, Asn, Ala, Gly, N-Me-Gln, Aib or Anb;

$A^{35}$ is Arg, Lys, homo-Arg, diethyl-homo-Arg, Lys-ϵ-NH-$R^5$, Cys or Orn; and $A^{36}$ is an aromatic amino acid or Cys;

where $R^5$ for each occurrence is independently selected from the group consisting of H, $(C_1-C_{10})$alkyl and $(C_6-C_{18})$ aryl.

15. A compound according to claim 14 of the formula N-α-Ac[Fla$^{27}$]PYY(25–36)-NH$_2$ or N-α-Ac-[Fla$^{27}$]PYY(22–36)-NH$_2$ or a pharmaceutically acceptable salt thereof.

16. A pharmaceutical composition comprising a compound of claim 13 or a pharmaceutically acceptable salt thereof, and a pharmaceutically acceptable carrier.

17. A method of decreasing excess intestinal water and electrolyte secretion in a mammal in need thereof, said method comprising administering to said mammal an effective amount of a compound of claim 13 or a pharmaceutically acceptable salt thereof.

18. A method of regulating cell proliferation in a mammal in need thereof, said method comprising administering to said mammal an effective amount of a compound of claim 13 or a pharmaceutically acceptable salt thereof.

19. A method of claim 18, wherein said cell is a gastrointestinal cell.

20. A method of claim 18, wherein said cell is an epithelial cell.

21. A method of augmenting nutrient transport in a mammal in need thereof, said method comprising administering to said mammal an effective amount of a compound of claim 13 or a pharmaceutically acceptable salt thereof.

22. A method of regulating lipolysis in a mammal in need thereof, said method comprising administering to said mammal an effective amount of a compound of claim 13 or a pharmaceutically acceptable salt thereof.

23. A method of regulating blood flow in a mammal in need thereof, said method comprising administering to said mammal an effective amount of a compound of claim 13 or a pharmaceutically acceptable salt thereof.

24. A C-terminal methyl ester peptide selected from the group consisting of 1

```
                                                 (SEQ. ID. NO. 11)
H-Ile-Asn-Pro-Ile-Tyr-Arg-Leu-Arg-Tyr-OMe, (SEQ. ID. NO. 12)
H-Ile-Asn-Pro-Cys-Tyr-Arg-Leu-Arg-Tyr-OMe
                  |
H-Ile-Asn-Pro-Cys-Tyr-Arg-Leu-Arg-Tyr-OMe, (SEQ. ID. NO. 13)
H-Cys-Tyr-Arg-Leu-Arg-Tyr-OMe
    |
H-Cys-Tyr-Arg-Leu-Arg-Tyr-OMe, (SEQ. ID. NO. 14)
H-Ile-Asn-Pro-NH-CH-CO-Tyr-Arg-Leu-Arg-Tyr-OMe
                 |
               (CH2)4
                 |
H-Ile-Asn-Pro-NH-CH-CO-Tyr-Arg-Leu-Arg-Tyr-OMe,
1

H-NH-CH-CO-Tyr-Arg-Leu-Arg-Tyr-OMe
           |
         (CH2)4
           |
       H-NH-CH-CO-Tyr-Arg-Leu-Arg-Tyr-OMe
```

H-(Tyr-Arg-Leu-Arg-Tyr)$_2$-OMe, (SEQ. ID. NO. 16); and pharmaceutically acceptable salts thereof.

25. A C-terminal amidated peptide selected from the group consisting of
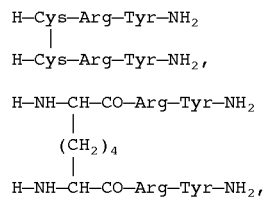
H-(Arg-Tyr)$_2$—NH$_2$, (SEQ. ID. NO. 20);
and pharmaceutically acceptable salts thereof.
26. The compound of the formula
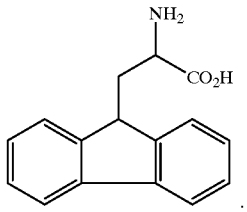
* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 36 amino acids
      (B) TYPE: amino acid
      (D) TOPOLOGY: linear (ii) MOLECULE TYPE: peptide (xi) SEQUENCE DESCRIPTION: SEQ ID NO:1:

```
Tyr Pro Ala Lys Pro Glu Ala Pro Gly Glu Asp Ala Ser Pro Glu
 1               5                  5                  15

Glu Leu Ser Arg Tyr Tyr Ala Ser Leu Arg His Tyr Leu Asn Leu
                20                  25                  30

Val Thr Arg Gln Arg Tyr
                35
```

(2) INFORMATION FOR SEQ ID NO: 2:

(i) SEQUENCE CHARACTERISTICS:
      (A) LENGTH: 36 amino acids
      (B) TYPE: amino acid
      (D) TOPOLOGY: linear (ii) MOLECULE TYPE: peptide (xi) SEQUENCE DESCRIPTION: SEQ ID NO:2:

```
Tyr Pro Ile Lys Pro Glu Ala Pro Gly Glu Asp Ala Ser Pro Glu
 1               5                  10                 15

Glu Leu Asn Arg Tyr Tyr Ala Ser Leu Arg His Tyr Leu Asn Leu
                20                  25                  30

Val Thr Arg Gln Arg Tyr
                35
```

(2) INFORMATION FOR SEQ ID NO: 3:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (B) LOCATION: 1...1
      (D) OTHER INFORMATION: the a-amino group of Ala at position
          1 is acetylated
      (B) LOCATION: 3...3
      (D) OTHER INFORMATION: Xaa at position 3 is norleucine
      (B) LOCATION: 7...7
      (D) OTHER INFORMATION: Xaa at position 7 is norleucine
      (B) LOCATION: 9...9
      (D) OTHER INFORMATION: Xaa at position 9 is norleucine
      (B) LOCATION: 10...10
      (D) OTHER INFORMATION: Xaa at position 10 is norvaline
      (B) LOCATION: 14...15
      (D) OTHER INFORMATION: the bond between Arg at position 14
          and Tyr at position 15 is a reduced peptide bond, i.e.,
          -CH2-NH-; and Tyr at position 15 is amidated (xi) SEQUENCE DESCRIPTION: SEQ ID NO:3:

Ala Ser Xaa Arg His Trp Xaa Asn Xaa Xaa Thr Arg Gln Arg Tyr
1               5                   10                  15

(2) INFORMATION FOR SEQ ID NO: 4:

(i) SEQUENCE CHARACTERISTICS:
        (A) LENGTH:  15 amino acids
        (B) TYPE:  amino acid
        (D) TOPOLOGY:  linear (ii) MOLECULE TYPE:  peptide (ix) FEATURE:
        (B) LOCATION: 1. . . 1
        (D) OTHER INFORMATION:  the a-amino group of Ala at
            position 1 is acetylated
        (B) LOCATION: 3. . . 3
        (D) OTHER INFORMATION:  Xaa at position 3 is norleucine
        (B) LOCATION: 7. . . 7
        (D) OTHER INFORMATION:  Xaa at position 7 is norleucine
        (B) LOCATION: 10. . . 10
        (D) OTHER INFORMATION:  Xaa at position 10 is norvaline
        (B) LOCATION: 14. . . 15
        (D) OTHER INFORMATION: the bond between Arg at position 14
            and Tyr at position 15 is a reduced peptide bond, i.e.,
            -CH2-NH-, and Tyr at position 15 is amidated (xi) SEQUENCE DESCRIPTION:  SEQ ID NO:4:

Ala Ser Xaa Arg His Trp Xaa Asn Trp Xaa Thr Arg Gln Arg Tyr
1               5                   10                  15

(2) INFORMATION FOR SEQ ID NO: 5:

(i) SEQUENCE CHARACTERISTICS:
        (A) LENGTH:  15 amino acids
        (B) TYPE:  amino acid
        (D) TOPOLOGY:  linear (ii) MOLECULE TYPE:  peptide (ix) FEATURE:
        (B) LOCATION: 1. . . 1
        (D) OTHER INFORMATION:  the a-amino group of Ala at
            position 1 is acetylated
        (B) LOCATION: 3. . . 3
        (D) OTHER INFORMATION:  Xaa at position 3 is norleucine
        (B) LOCATION: 7. . . 7
        (D) OTHER INFORMATION:  Xaa at position 7 is norleucine
        (B) LOCATION: 9. . . 9
        (D) OTHER INFORMATION:  Xaa at position 9 is norleucine
        (B) LOCATION: 10. . . 10
        (D) OTHER INFORMATION:  Xaa at position 10 is norvaline
        (B) LOCATION: 14. . . 15
        (D) OTHER INFORMATION: the bond between Arg at position 14
            and Tyr atp osition 15 is a reduced peptide bond, i.e.,
            -CH2-NH-, and Tyr at position 15 is amidated (xi) SEQUENCE DESCRIPTION:  SEQ ID NO:5:

Ala Ser Xaa Arg His Phe Xaa Asn Xaa Xaa Thr Arg Gln Arg Tyr
1               5                   10                  15

(2) INFORMATION FOR SEQ ID NO: 6:

(i) SEQUENCE CHARACTERISTICS:
        (A) LENGTH:  15 amino acids
        (B) TYPE:  amino acid
        (D) TOPOLOGY:  linear (ii) MOLECULE TYPE:  peptide (ix) FEATURE:

```
        (B) LOCATION: 1. . . 1
        (D) OTHER INFORMATION: the a-amino group of Ala at
            position 1 is acetylated
        (B) LOCATION: 3. . . 3
        (D) OTHER INFORMATION: Xaa at position 3 is norleucine
        (B) LOCATION: 7. . . 7
        (D) OTHER INFORMATION: Xaa at position 7 is norleucine
        (B) LOCATION: 10. . . 10
        (D) OTHER INFORMATION: Xaa at position 10 is norvaline
        (B) LOCATION: 14. . . 15
        (D) OTHER INFORMATION: the bond between Arg at position 14
            and Tyr at position 15 is a reduced peptide bond, i.e.,
            -CH2-NH-, and Tyr at position 15 is amidated (xi) SEQUENCE DESCRIPTION: SEQ ID NO:6:

Ala Ser Xaa Arg His Phe Xaa Asn Trp Xaa Thr Arg Gln Arg Tyr
 1           5                   10                  15

(2) INFORMATION FOR SEQ ID NO: 7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (B) LOCATION: 1. . . 1
        (D) OTHER INFORMATION: the a-amino group of Arg at
            position 1 is acetylated
        (B) LOCATION: 11. . . 12
        (D) OTHER INFORMATION: the bond between Arg at position 11
            and Tyr at position 12 is a reduced peptide bond, i.e.,
            -CH2-NH-, and Tyr at position 12 is amidated (xi) SEQUENCE DESCRIPTION: SEQ ID NO:7:

Arg His Tyr Leu Asn Trp Val Thr Arg Gln Arg Tyr
 1           5                   10

(2) INFORMATION FOR SEQ ID NO: 8:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (B) LOCATION: 1. . . 1
        (D) OTHER INFORMATION: the a-amino group of Arg at
            position 1 is acetylated
        (B) LOCATION: 11. . . 12
        (D) OTHER INFORMATION: the bond between Arg at position 11
            and Tyr at position 12 is a reduced peptide bond, i.e.,
            -CH2-NH-, and Tyr at position 12 is amidated (xi) SEQUENCE DESCRIPTION: SEQ ID NO:8:

Arg His Tyr Leu Asn Trp Val Thr Arg Gln Arg Tyr
 1           5                   10

(2) INFORMATION FOR SEQ ID NO: 9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (B) LOCATION: 1. . . 1
```

(D) OTHER INFORMATION: the a-amino group of Ala at
                position 1 is acetylated
            (B) LOCATION: 3...3
            (D) OTHER INFORMATION: Xaa at position 3 is norleucine
            (B) LOCATION: 7...7
            (D) OTHER INFORMATION: Xaa at position 7 is norleucine
            (B) LOCATION: 10...10
            (D) OTHER INFORMATION: Xaa at position 10 is norvaline
            (B) LOCATION: 14...15
            (D) OTHER INFORMATION: the bond between Arg at position 14
                and Tyr at position 15 is a reduced peptide bond, i.e.,
                -CH2-NH-, and Tyr at position 15 is amidated (xi) SEQUENCE DESCRIPTION: SEQ ID NO:9:

Ala Ser Xaa Arg His Tyr Xaa Asn Trp Xaa Thr Arg Gln Arg Tyr
 1               5                  10                  15

(2) INFORMATION FOR SEQ ID NO: 10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
            (B) LOCATION: 1...1
            (D) OTHER INFORMATION: the a-amino group of Ala at
                position 1 is acetylated
            (B) LOCATION: 7...7
            (D) OTHER INFORMATION: Xaa at position 7 is norleucine
            (B) LOCATION: 10...10
            (D) OTHER INFORMATION: Xaa at position 10 is norvaline
            (B) LOCATION: 14...15
            (D) OTHER INFORMATION: the bond between Arg at position 14
                and Tyr atp osition 15 is a reduced peptide bond, i.e.,
                -CH2-NH-, and Tyr at position 15 is amidated (xi) SEQUENCE DESCRIPTION: SEQ ID NO:10:

Ala Ser Leu Arg His Tyr Xaa Asn Trp Xaa Thr Arg Gln Arg Tyr
 1               5                  10                  15

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
            (B) LOCATION: 9...9
            (D) OTHER INFORMATION: the carboxyl group of Tyr at
                position 9 is esterified as a methyl ester (xi) SEQUENCE DESCRIPTION: SEQ ID NO:11:

Ile Asn Pro Ile Tyr Arg Leu Arg Tyr
 1               5

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
            (B) LOCATION: 9...9
            (D) OTHER INFORMATION: the carboxyl group of Tyr at

```
           position 9 is esterified as a methyl ester, and the
           peptide is linked to another identical peptide via a
           disulfide bond formed between each Cys at
           position 4

(xi) SEQUENCE DESCRIPTION: SEQ ID NO:12:

Ile Asn Pro Cys Tyr Arg Leu Arg Tyr
1               5

(2) INFORMATION FOR SEQ ID NO: 13:

(i) SEQUENCE CHARACTERISTICS:
        (A) LENGTH:  6 amino acids
        (B) TYPE:  amino acid
        (D) TOPOLOGY:  linear (ii) MOLECULE TYPE:  peptide (ix) FEATURE:
        (B) LOCATION: 6. . . 6
        (D) OTHER INFORMATION: :  the carboxyl group of Tyr at
            position 6 is esterified as a methyl ester, and the
            peptide is linked to another identical peptide via a
            disulfide bond formed between each Cys at position 1

(xi) SEQUENCE DESCRIPTION:  SEQ ID NO:13:

Cys Tyr Arg Leu Arg Tyr
1               5

(2) INFORMATION FOR SEQ ID NO: 14:

(i) SEQUENCE CHARACTERISTICS:
        (A) LENGTH:  9 amino acids
        (B) TYPE:  amino acid
        (D) TOPOLOGY:  linear (ii) MOLECULE TYPE:  peptide (ix) FEATURE:
        (B) LOCATION: 9. . . 9
        (D) OTHER INFORMATION:  the carboxyl group of Tyr at
            position 9 is esterified as a methyl ester (xi) SEQUENCE DESCRIPTION:  SEQ ID NO:14:

Ile Asn Pro Xaa Tyr Arg Leu Arg Tyr
1               5

(2) INFORMATION FOR SEQ ID NO: 15:

(i) SEQUENCE CHARACTERISTICS:
        (A) LENGTH:  6 amino acids
        (B) TYPE:  amino acid
        (D) TOPOLOGY:  linear (ii) MOLECULE TYPE:  peptide (ix) FEATURE:
        (B) LOCATION: 6. . . 6
        (D) OTHER INFORMATION:  the carboxyl group of Tyr at
            position 6 is esterified as a methyl ester (xi) SEQUENCE DESCRIPTION:  SEQ ID NO:15:

Xaa Tyr Arg Leu Arg Tyr
1               5

(2) INFORMATION FOR SEQ ID NO: 16:

(i) SEQUENCE CHARACTERISTICS:
        (A) LENGTH:  10 amino acids
        (B) TYPE:  amino acid
        (D) TOPOLOGY:  linear
```

(ii) MOLECULE TYPE:  peptide (ix) FEATURE:
              (B) LOCATION: 10. . . 10
              (D) OTHER INFORMATION:  the carboxyl group of Tyr at
                  position 10 is sterified as a methyl ester (xi) SEQUENCE DESCRIPTION:  SEQ ID NO:16:

Tyr  Arg  Leu  Arg  Tyr  Tyr  Arg  Leu  Arg  Tyr
 1              5                        10

(2) INFORMATION FOR SEQ ID NO: 17:

(i) SEQUENCE CHARACTERISTICS:
              (A) LENGTH:  12 amino acids
              (B) TYPE:  amino acid
              (D) TOPOLOGY:  linear (ii) MOLECULE TYPE:  peptide (ix) FEATURE:
              (B) LOCATION: 3. . . 3
              (D) OTHER INFORMATION:  Xaa at position 3 is
                  9-fluorenylalanine
              (B) LOCATION: 12. . . 12
              (D) OTHER INFORMATION:  Tyr at position 12 is amidated (xi) SEQUENCE DESCRIPTION:  SEQ ID NO:17:

Arg  His  Xaa  Leu  Asn  Leu  Val  Thr  Arg  Gln  Arg  Tyr
 1              5                        10

(2) INFORMATION FOR SEQ ID NO: 18:

(i) SEQUENCE CHARACTERISTICS:
              (A) LENGTH:  15 amino acids
              (B) TYPE:  amino acid
              (D) TOPOLOGY:  linear (ii) MOLECULE TYPE:  peptide (ix) FEATURE:
              (B) LOCATION: 6. . . 6
              (D) OTHER INFORMATION:  Xaa at position 6 is
                  9-fluorenylalanine
              (B) LOCATION: 15. . . 15
              (D) OTHER INFORMATION:  Tyr at position 15 is amidated (xi) SEQUENCE DESCRIPTION:  SEQ ID NO:18:

Ala  Ser  Leu  Arg  His  Xaa  Leu  Asn  Leu  Val  Thr  Arg  Gln  Arg  Tyr
 1              5                        10                       15

(2) INFORMATION FOR SEQ ID NO: 19:

(i) SEQUENCE CHARACTERISTICS:
              (A) LENGTH:  9 amino acids
              (B) TYPE:  amino acid
              (D) TOPOLOGY:  linear (ii) MOLECULE TYPE:  peptide (ix) FEATURE:
              (B) LOCATION: 4. . . 4
              (D) OTHER INFORMATION:  Xaa at position 4 is 1,2-diamino
                  propionic acid
              (B) LOCATION: 4. . . 4
              (D) OTHER INFORMATION:  Xaa at position 4 is esterified as
                  a methyl ester, and the peptide is linked to another
                  identical peptide via two amino bonds, each of which is
                  formed between the side chain amino group of Xaa at
                  position 4 and the side chain carboxyl group
                  of Glu at position 2

-continued

```
    (xi) SEQUENCE DESCRIPTION: SEQ ID NO:19:

Ile Glu Pro Xaa Tyr Arg Leu Arg Tyr
1               5

(2) INFORMATION FOR SEQ ID NO: 20:

(i) SEQUENCE CHARACTERISTICS:
        (A) LENGTH:  4 amino acids
        (B) TYPE:    amino acid
        (D) TOPOLOGY: linear (ii) MOLECULE TYPE: peptide (xi) SEQUENCE DESCRIPTION: SEQ ID NO:20:

Arg Tyr Arg Tyr
```